US010653686B2

(12) United States Patent
Azhir

(10) Patent No.: US 10,653,686 B2
(45) Date of Patent: May 19, 2020

(54) COMPOSITIONS AND METHODS FOR TREATMENT OF SYMPTOMS IN PARKINSON'S DISEASE PATIENTS

(71) Applicant: Parkinson's Institute, Sunnyvale, CA (US)

(72) Inventor: Arasteh Ari Azhir, Los Altos, CA (US)

(73) Assignee: PARKINSON'S INSTITUTE, Sunnyvale, CA (US)

( * ) Notice: Subject to any disclaimer, the term of this patent is extended or adjusted under 35 U.S.C. 154(b) by 0 days.

(21) Appl. No.: 15/659,383

(22) Filed: Jul. 25, 2017

(65) Prior Publication Data
US 2019/0054078 A1 Feb. 21, 2019

Related U.S. Application Data

(63) Continuation of application No. 14/838,208, filed on Aug. 27, 2015, now abandoned, which is a continuation of application No. 13/541,333, filed on Jul. 3, 2012, now abandoned.

(60) Provisional application No. 61/504,974, filed on Jul. 6, 2011.

(51) Int. Cl.
| A61K 31/465 | (2006.01) |
| A61K 9/20 | (2006.01) |
| A61K 9/48 | (2006.01) |
| A61K 31/198 | (2006.01) |

(52) U.S. Cl.
CPC .............. *A61K 31/465* (2013.01); *A61K 9/20* (2013.01); *A61K 9/2004* (2013.01); *A61K 9/2009* (2013.01); *A61K 9/2031* (2013.01); *A61K 9/2054* (2013.01); *A61K 9/2068* (2013.01); *A61K 9/48* (2013.01); *A61K 9/4891* (2013.01); *A61K 31/198* (2013.01)

(58) Field of Classification Search
CPC .. A61K 9/2031; A61K 9/2054; A61K 9/2009; A61K 9/2004; A61K 9/20; A61K 9/4891; A61K 9/2068; A61K 31/465; A61K 31/198
See application file for complete search history.

(56) References Cited

U.S. PATENT DOCUMENTS

| 2,183,482 | A | 12/1939 | Kurkjian |
| 3,845,217 | A | 10/1974 | Ferno et al. |
| 4,321,387 | A | 3/1982 | Chavdarian et al. |
| 4,327,725 | A | 5/1982 | Cortese et al. |
| 4,332,945 | A | 6/1982 | Edwards |
| 4,379,454 | A | 4/1983 | Campbell et al. |
| 4,545,990 | A | 10/1985 | Le Foyer de Costil et al. |
| 4,579,858 | A | 4/1986 | Ferno et al. |
| 4,590,278 | A | 5/1986 | Edwards |
| 4,708,716 | A | 11/1987 | Sibalis |
| 4,772,263 | A | 9/1988 | Dorman et al. |
| 4,806,356 | A | 2/1989 | Shaw |
| 4,853,854 | A | 8/1989 | Behar et al. |
| 4,885,154 | A | 12/1989 | Cormier et al. |
| 4,908,213 | A | 3/1990 | Govil et al. |
| 4,917,676 | A | 4/1990 | Heiber et al. |
| 4,917,895 | A | 4/1990 | Lee et al. |
| 4,920,989 | A | 5/1990 | Rose et al. |
| 4,952,928 | A | 8/1990 | Carroll et al. |
| 4,953,572 | A | 9/1990 | Rose et al. |
| 5,000,956 | A | 3/1991 | Amkraut et al. |
| 5,013,293 | A | 5/1991 | Sibalis |
| 5,049,387 | A | 9/1991 | Amkraut |
| 5,069,904 | A | 12/1991 | Masterson |
| 5,097,834 | A | 3/1992 | Skrabal |
| 5,120,545 | A | 6/1992 | Ledger et al. |
| 5,130,139 | A | 7/1992 | Cormier et al. |
| 5,149,538 | A | 9/1992 | Granger et al. |
| 5,149,719 | A | 9/1992 | Ferber et al. |
| 5,212,188 | A | 5/1993 | Caldwell et al. |
| 5,221,254 | A | 6/1993 | Phipps |
| 5,227,391 | A | 7/1993 | Caldwell et al. |
| 5,232,704 | A | 8/1993 | Franz et al. |
| 5,232,933 | A | 8/1993 | Lippiello et al. |
| 5,236,714 | A | 8/1993 | Lee et al. |
| 5,242,934 | A | 9/1993 | Lippiello et al. |
| 5,242,941 | A | 9/1993 | Lewy et al. |
| 5,248,690 | A | 9/1993 | Caldwel et al. |
| 5,252,604 | A | 10/1993 | Nagy et al. |
| 5,262,165 | A | 11/1993 | Govil et al. |
| 5,273,755 | A | 12/1993 | Venkatraman et al. |

(Continued)

FOREIGN PATENT DOCUMENTS

| AU | 662877 B | 9/1995 |
| BE | 899037 A | 6/1984 |

(Continued)

OTHER PUBLICATIONS

Abood et al.; Structure-activity studies of carbamate and other esters: agonists and antagonists to nicotine; Pharmacology Biochemistry and Behavior; 30(2); pp. 403-408; Jun. 1988.

Ahlskog et al.; Frequency of levodopa-related dyskinesias and motor fluctuations as estimated from the cumulative literature; Movement Disorders; 16(3); pp. 448-458; May 1, 2001.

Angulo et al.; Oral nicotine in treatment of primary sclerosing cholangitis: a pilot study; Digestive diseases and sciences; 44(3); pp. 602-607; Mar. 1, 1999.

Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filing date and any foreign priority date) 1981.

Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.

(Continued)

*Primary Examiner* — Blessing M Fubara
(74) *Attorney, Agent, or Firm* — Wilson Sonsini Goodrich & Rosati

(57) ABSTRACT

The invention provides dosage forms and methods utilizing nicotine to treat symptoms of a neurologic disorder. In some embodiments, the invention provides compositions for treatment of gait and balance problems associated with Parkinson's Disease.

12 Claims, 5 Drawing Sheets

(56) References Cited

U.S. PATENT DOCUMENTS

| | | |
|---|---|---|
| 5,273,756 A | 12/1993 | Fallon et al. |
| 5,304,739 A | 4/1994 | Klug et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,492,399 B1 | 12/2002 | Dull et al. |
| 6,539,250 B1 | 3/2003 | Bettinger |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,988,660 B2 | 8/2011 | Byland et al. |
| 8,021,334 B2 | 9/2011 | Shekalim |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |

(56) References Cited

U.S. PATENT DOCUMENTS

| | | |
|---|---|---|
| 8,741,336 B2 | 6/2014 | DiPierro et al. |
| 8,747,348 B2 | 6/2014 | Yodfat et al. |
| 8,753,315 B2 | 6/2014 | Alferness et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,114,240 B2 | 8/2015 | Horstmann et al. |
| 9,155,712 B2 | 10/2015 | Kanios et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| RE46,217 E | 11/2016 | Huang et al. |
| 9,549,903 B2 | 1/2017 | Hille et al. |
| 9,555,226 B2 | 1/2017 | Zumbrunn et al. |
| 9,555,227 B2 | 1/2017 | Dipierro |
| 9,655,843 B2 | 5/2017 | Finn et al. |
| 9,669,199 B2 | 6/2017 | DiPierro et al. |
| 9,700,552 B2 | 7/2017 | Weimann |
| 9,717,698 B2 | 8/2017 | Horstmann et al. |
| 9,795,681 B2 | 10/2017 | Abreu |
| 10,004,447 B2 | 6/2018 | Shen et al. |
| 10,034,841 B2 | 7/2018 | Müller et al. |
| 10,105,487 B2 | 10/2018 | DiPierro et al. |
| 10,143,687 B2 * | 12/2018 | Azhir .................. A61K 31/465 |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2006/0024358 A1 | 2/2006 | Santini et al. |
| 2006/0036209 A1 | 2/2006 | Subramony et al. |
| 2006/0122577 A1 | 6/2006 | Poulsen et al. |
| 2006/0167039 A1 | 7/2006 | Nguyen et al. |
| 2006/0184093 A1 | 8/2006 | Phipps et al. |
| 2006/0188859 A1 | 8/2006 | Yakobi |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0149952 A1 | 6/2007 | Bland et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0260825 A1 * | 10/2008 | Quik .................. A61K 31/198 424/472 |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0024004 A1 | 1/2009 | Yang |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2010/0003653 A1 | 1/2010 | Brown |
| 2010/0068250 A1 | 3/2010 | Anderson et al. |
| 2010/0114008 A1 | 5/2010 | Marchitto et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0241446 A1 | 10/2011 | Tucholski |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 * | 11/2011 | Brinkley .............. A61K 9/0056 424/499 |
| 2011/0275987 A1 | 11/2011 | Caffey et al. |
| 2012/0046644 A1 | 2/2012 | Ziaie et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |

(56) References Cited

U.S. PATENT DOCUMENTS

| | | |
|---|---|---|
| 2012/0316896 A1 | 12/2012 | Rahman et al. |
| 2012/0329017 A1 | 12/2012 | Pham |
| 2013/0017259 A1 | 1/2013 | Azhir |
| 2013/0123719 A1 | 5/2013 | Mao et al. |
| 2013/0158430 A1 | 6/2013 | Aceti et al. |
| 2013/0178826 A1 | 7/2013 | Li |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0345633 A1 | 12/2013 | Chong |
| 2014/0046288 A1 | 2/2014 | Geipel et al. |
| 2014/0073883 A1 | 3/2014 | Rao et al. |
| 2014/0100241 A1 | 4/2014 | Slater et al. |
| 2014/0200525 A1 | 7/2014 | DiPierro |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0303574 A1 | 10/2014 | Knutson |
| 2015/0273148 A1 | 10/2015 | Sexton et al. |
| 2016/0220553 A1 | 8/2016 | Azhir |
| 2016/0220798 A1 | 8/2016 | Netzel et al. |
| 2016/0235732 A1 | 8/2016 | Quik et al. |
| 2016/0235916 A1 | 8/2016 | Edwards et al. |
| 2016/0310664 A1 | 10/2016 | McKenzie et al. |
| 2017/0100572 A1 | 4/2017 | Zumbrunn et al. |
| 2017/0100573 A1 | 4/2017 | DiPierro |
| 2017/0182299 A1 | 6/2017 | DiPierro et al. |
| 2017/0224911 A1 | 8/2017 | Dipierro et al. |
| 2018/0110768 A1 | 4/2018 | Quik et al. |
| 2018/0117291 A1 | 5/2018 | Netzel et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 0314528 B1 | 12/1992 |
| EP | 0354554 B1 | 1/1994 |
| EP | 0726005 A1 | 8/1996 |
| EP | 0612525 B1 | 9/2001 |
| EP | 1815784 A1 | 8/2007 |
| EP | 1977746 B1 | 7/2014 |
| EP | 1662989 B1 | 9/2014 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | 09512006 A | 12/1997 |
| JP | 2002092180 A | 3/2002 |
| JP | 2005525147 A | 8/2005 |
| JP | 2009544338 A | 12/2009 |
| WO | WO86/07269 A1 | 12/1986 |
| WO | WO88/003803 A1 | 6/1988 |
| WO | WO91/14441 A1 | 10/1991 |
| WO | WO94/010987 A1 | 5/1994 |
| WO | WO95/06497 A1 | 3/1995 |
| WO | WO97/11741 A1 | 4/1997 |
| WO | WO97/18782 A1 | 5/1997 |
| WO | WO97/028801 A1 | 8/1997 |
| WO | WO97/034605 A1 | 9/1997 |
| WO | WO97/042941 A2 | 11/1997 |
| WO | WO98/46093 A1 | 10/1998 |
| WO | WO99/066916 A1 | 12/1999 |
| WO | WO00/035279 A1 | 6/2000 |
| WO | WO00/035456 A1 | 6/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2013/093666 A1 | 6/2013 |
| WO | WO2013/168068 A1 | 11/2013 |
| WO | WO2014/001877 A1 | 1/2014 |

OTHER PUBLICATIONS

Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.

Bordia et al.; Partial recovery of striatal nicotinic receptors in l-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.

Bove et al.; Toxin-induced models of Parkinson's disease; NeuroRx; 2(3); pp. 484-494; Jul. 31, 2005.

Brotchie et al.; Levodopa-induced dyskinesia in Parkinson's disease; Journal of Neural Transmission; 112(3); pp. 359-391; Mar. 1, 2005.

Bruguerolle; Chronopharmacokinetics; Clin Pharmacokinet; 35(2); pp. 83-94; Aug. 1998.

Calabres et al.; Levodopa-induced dyskinesias inpatients with parkinson's disease: filling the bench-to-bedside gap; The Lancet Neurology; 9(11); pp. 1106-1117; Nov. 1, 2010.

Chen et al.; Enhanced striatal opioid receptor-mediated G-protein activation in L-DOPA-treated dyskinetic monkeys; Neuroscience; 132(2); pp. 409-420; Dec. 31, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86(1):109-127; Apr. 8, 2008.

De La Fuente et al.; The placebo effect in Parkinson's disease; Trends in Neuroscience; 25(6); pp. 302-306; Jun. 1, 2002.

Di Monte et al.; Relationship among nigrostriatal denervation, parkinsonism, and dyskinesias in the MPTP primate model; Movement Disorders; 15(3); pp. 459-466; May 1, 2000.

Dockser-Marcus, A.; New research shows drugs work best at certain times; The Wall Street Journal; 6 pgs.; May 27, 2003; (http://www.wsj.com/articles/SB1053973124865 08700).

Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.

Domino et al.; Nicotine alone and in combination with L-DOPA methyl ester or the D2 agonist N-0923 in MPTP-induced chronic hemiparkinsonian monkeys; Experimental Neurology; 158(2); pp. 414-421; Aug. 31, 1999.

(56) References Cited

OTHER PUBLICATIONS

Dutil; Benzoyl Peroxide: Enhancing antibiotic efficacy in acne management; Skin Therapy Letter; 15(1); pp. 5-7; Nov./Dec. 2010.
Ebersbach et al.; Worsening of motor performance in patients with Parkinson's disease following transdermal nicotine administration; Movement Disorders; 14(6); pp. 1011-1013; Nov. 1, 1999.
Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.
Fagerstrom et al.; Nicotine may relieve symptoms of Parkinson's disease; Psychopharmacology; 116(1); pp. 117-119; Sep. 16, 1994.
Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.
Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.
Gennaro (Editor); Remington: The Science and Practice of Pharmacy; 19th Ed.; Mack Publishing Co.; Easton, PA; p. 1582-1584; Jun. 1995.
Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.
Gora; Nicotine transdermal systems; The Annals of Pharmacotherapy; 27(6); pp. 742-750; Jun. 1993.
Gotti et al.; Brain nicotinic acetylcholine receptors: native subtypes and their relevance; Treands in Pharmacological Sciences; 27(9); pp. 482-491; Sep. 30, 2006.
Green et al.; An oral formulation of nicotine for release and absorption in the colon: its development and pharmacokinetics. British Journal of Clinical Pharmacology; 48(4); pp. 485-493; Oct. 1999.
Gries et al.; Importance of Chronopharmacokinetics in Design and Evaluation of Transdermal Drug Delivery Systems; J Pharmacol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.
He et al.; Autoradiographic analysis of dopamine receptor-stimulated [35S]GTPtS binding in rat striatum; Brain Research; 885(1); pp. 133-136; Dec. 1, 2000.
He et al; Autoradiographic analysis of N-methyl-D-aspartate receptor binding in monkey brain: Effects of l-methyl-4-phenyl-l,2,3,6-tetrahydropyridine andlevodopa treatment; Neuroscience; 99(4); pp. 697-704; Aug. 23, 2000.
Hrushesky; Temporally optimizable delivery systems: sine qua non for the next therapeutic revolution; J Cont Rel; 19(1-3); pp. 363-368; Mar. 1992.
Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.
Huang et al.; Inhibitory effects of curcumin on in vitro lipoxygenase and cyclooxygenase activities in mouse epidermis; Cancer Res; 51(3); pp. 813-819; Feb. 1991.
Hukkanen et al.; Metabolism and disposition kinetics of nicotine; Pharmacological Reviews; 57(1); pp. 79-115; Mar. 1, 2005.
Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.

Jarvik et al.; Inhibition of cigarette smoking by orally administered nicotine; Clinical Pharmacology and Therapeutics; 11(4); pp. 574-576; Jul. 1, 1970.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Jeyarasasingam et al.; Stimulation of non-o7 nicotinic receptors partially protects dopaminergic neurons from 1-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11(6); pp. 1173-1176; Apr. 27, 2000.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.
Kelton et al.; The effects of nicotine on Parkinson's disease; Brain Cognition; 43(1-3); pp. 274-282; Jun. 2000.
Kiwi Drug; Buy nicorette microtabs; 3 pages; retrieved from the internet (www.kiwidrug.com/search/nicorette_microtabs); on Jul. 26, 2018.
Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kulak et al.; 5-Iodo-A-85380 binds to oconotoxin Mil-sensitive nicotinic acetylcholine receptors (nAChRs) as well as o4j32* subtypes; Journal of Neurochemistry; 81(2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after 1-mefhyl-4-phenyl-1,2,3,6-tetrahydropyridine treatment is due to a decline in oconotoxin Mil sites; Molecular Pharmacology; 61(1); pp. 230-238; Jan. 1, 2002.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; (year of pub. sufficiently earlier than effective US filing date and any foreign priority date) 1997.
Lai et al.; Long-term nicotine treatment decreases striatal a6* nicotinic acetylcholine receptor sites and function in mice; Molecular Pharmacology; 67(5); pp. 1639-1647; May 1, 2005.
Lai et al.; Selective recovery of striatal 1251-a-conotoxinMII nicotinic receptors after nigrostriatal damage in monkeys; Neuroscience; 127(2); pp. 399-408; Dec. 31, 2004.
Lamberg; Chronotherapeutics: Implications for drug therapy; American Pharmacy; NS31(11); pp. 20-23; Nov. 1991.
Langston et al.; Investigating levodopa-induced dyskinesias in the parkinsonian primate; Annals of Neurology; 47(4 Suppl 1); pp. S79-S88; Apr. 2000.
Laser et al.; A review of micropumps; J. of Micromech. and Microeng.; 14; pp. R35-R64; Apr. 2004.
Lee et al.; A comprehensive review of opioid-induced hyperalgesia; Pain Physician; 14; pp. 145-161; Mar. 2011.
Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.
Lemmer; The clinical relevance of chronopharmacology in therapeutics; Pharmacological Research; 33(2); pp. 107-115; Feb. 1996.

(56) References Cited

OTHER PUBLICATIONS

LeWitt et al.; New developments in levodopa therapy; Neurology; 62(No. 1, Suppl. 1); pp. S9-S16; Jan. 2004.
Lieber Man; Compressed tablets by direct compression; Pharmaceutical Dosage forms; vol. 1, 2nd ed.; Marcel Dekker Inc.; pp. 195-246; (year of pub. sufficiently earlier than effective US filing date and any foreign priority date) 1989.
Lieberman; Compression—coated and layer tablets; Pharmaceutical Dosage forms; vol. 1, 2nd ed.; Marcel Dekker Inc.; pp. 266-271; (year of pub. sufficiently earlier than effective US filing date and any foreign priority date) 1989.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Matta et al.; Guidelines on nicotine dose selection for in vivo research; Psychopharmacology (Berl.); 190(3); pp. 269-319; Feb. 1, 2007.
McCallum et al.; Decrease in alpha3*/alpha6* nicotinic receptors in monkey brain after nigrostriatal damage; Molecular Pharmacology; 68(3); pp. 737-746; Sep. 2005.
McCallum et al.; Compensation in pre-synaptic dopaminergic function following nigrostriatal damage in primates; Journal of Neurochemistry; 96(4); pp. 960-972; Feb. 1, 2006.
McCallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
McCallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket.se/SPC_PIL/Pdf/enhumpil/Nicorette%20Microtab%20Lemon%202mg%20sublingual%20tablet%20ENG.pdf.) Accessed Aug. 19, 2010.
Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.
Meissner et al.; Priorities in parkinson's disease research; Nature reviews Drug Discovery; 10(5); pp. 377-393; May 1, 2011.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
MERCK manual of therapy and diagnosis; 17th edition. Merck Research Laboratories; pp. 1466-1471; (year of pub. sufficiently earlier than effective US filing date and any foreign priority date) 1999.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; (year of pub. sufficiently earlier than effective US filing date and any foreign priority date) 2002.
Meshul et al.; Nicotine alters striatal glutamate function and decreases the apomorphine-induced contralateral rotations in 6-OHDA-lesioned rats; Experimental Neurology; 175(1); pp. 257-274; May 31, 2002.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16); pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
National Institute of Neurological Disorders and Stroke. Parkinson's Disease: Hope Through Research. 54 pages; Retrieved from the internet (https://catalog.ninds.nih.gov/pubstatic//15-139/15-139.pdf) on Jan. 15, 2018.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
Ohdo; Changes in toxicity and effectiveness with timing of drug administration: implications for drug safety; Drug Safety; 26(14); pp. 999-1010; Dec. 2003.
Olanow; The scientific basis for the current treatment of Parkinson's disease; Annu. Rev. Med.; 55; pp. 41-60; Feb. 18, 2004.
Olsson et al.; A valve-less planar pump in silicon; IEEE; The 8th International Conference on Solid-State Sensors and Actuators; vol. 2; pp. 291-294; Jun. 1995.
Olsson et al.; An improved valve-less pump fabricated using deep reactive ion etching; Proc. of the IEEE, 9th Int'l Workshop on MEMS; San Diego, CA; pp. 479-484; Feb. 11-15, 1996.
O'Neill et al.; The role of neuronal nicotinic acetylcholine receptors in acute and chronic neurodegeneration; Current Drug Targets-CNS and Neurological Disorders; 1(4); pp. 399-412; Aug. 1, 2002.
Parkinson Study Group; Levodopa and the progression of Parkinson's disease; N Engl J Med.; 351; pp. 2498-2508; Dec. 9, 2004.
Petzinger et al.; Reliability and validity of a new global dyskinesia rating scale in the MPTP-lesioned non-human primate; Movement Disorders; 16(2); pp. 202-207; Mar. 1, 2001.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; Chronic oral nicotine normalizes dopaminergic function and synaptic plasticity in l-methyl-4-phenyl-l,2,3,6-tetrahydropyridine-lesioned primates; The Journal ofNeuroscience; 26(17); pp. 4681-4689; Apr. 26, 2006.
Quik et al.; Chronic oral nicotine treatment protects against striatal degeneration in MPTP-treated primates; Journal of Neurochemistry; 98(6); pp. 1866-1875; Sep. 1, 2006.
Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.
Quik et al.; Differential declines in striatal nicotinic receptor subtype function after nigrostriatal damage in mice; Molecular Pharmacology; 63(5); pp. 1169-1179; May 1, 2003.
Quik et al.; Differential nicotinic receptor expression in monkey basal ganglia: Effects of nigrostriatal damage; Neuroscience; 112(3); pp. 619-630; Jul. 5, 2002.
Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.
Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.
Quik et al.; L-DOPA treatment modulates nicotinic receptors in monkey striatum; Mol Pharmacol; 64(3); pp. 619-628; Sep. 2003.
Quik et al.; Localization of nicotinic receptor subunit mRNAs in monkey brain by in situ hybridization; The Journal of Comparative Neurology; 425(1); pp. 58-69; Sep. 11, 2000.

(56) References Cited

OTHER PUBLICATIONS

Quik et al.; Loss of a-conotoxinMII- and A85380-sensitive nicotinic receptors in Parkinson's disease striatum; Journal of Neurochemistry; 88(3); pp. 668-679; Feb. 1, 2004.
Quik et al.; Nicotine administration reduces striatal MPP+ levels in mice; Brain Research; 917(2); pp. 219-224; Nov. 2, 2001.
Quik et al.; Nicotine and nicotinic receptors; relevance to Parkinson's disease; Neurotoxicology; 23(4-5); pp. 581-594; Oct. 2002.
Quik et al.; Nicotine and Parkinson's disease: implications for therapy; Movement Disorders; 23(12); pp. 1641-1652; (Author Manuscript); Sep. 1, 2008.
Quik et al.; Nicotine neuroprotection against nigrostriatal damage: importance of the animal model; Trends in Pharmacological sciences; 28(5); pp. 229-235; May 31, 2007.
Quik et al.; Nicotine reduces levodopa-induced dyskinesias in lesioned monkeys; Annals of neurology; 62(6); pp. 588-596; (Author Manuscript); Dec. 1, 2007.
Quik et al.; Nicotinic receptors and Parkinson's disease; European Journal of Pharmacology; 393(1); pp. 223-230; Mar. 30, 2000.
Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.
Quik et al.; Subunit composition of nicotinic receptors in monkey striatum: Effect of treatments with 1-methyl-4-phenyl-1,2,3,6-tetrahydropyridine or L-DOPA; Molecular Pharmacology; 67(1); pp. 32-41; Jan. 2005.
Quik et al.; Vulnerability of 125l-a-conotoxin Mil binding sites to nigrostriatal damage in monkey; The Journal of Neuroscience; 21(15); pp. 5494-5500; Aug. 1, 2001.
Quik; Smoking, nicotine and Parkinson's disease; Trends in Neurosciences; 27(9); pp. 561-568; Sep. 2004.
Redfern et al.; Circadian rhythms, jet lag, and chronobiotics: An overview; Chronobiology International; 11(4); pp. 253-265; Aug. 1994.
Reinberg; Concepts of Circadian Chronopharmacology; Annals of the New York Academy of Sciences; 618 (Temporal Control of Drug Delivery); pp. 102-115; Feb. 1991.
Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.
Samii et al.; Parkinson's disease; The Lancet; 363(9423); pp. 1783-1793; May 29, 2004.
Savitt et al.; Diagnosis and treatment of Parkinson disease: molecules to medicine; The Journal of Clinical Investigation; 116(7); pp. 1744-1754; Jul. 3, 2006.
Schapira; Disease modification in Parkinson's disease; The Lancet Neurology; 3(6); pp. 362-368; Jun. 30, 2004.
Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.
Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.
Schober et al.; Classic toxin-induced animal models of Parkinson's disease: 6-OHDA and MPTP; Cell and Tissue Research; 318(1); pp. 215-224; Oct. 1, 2004.
Shin et al.; Enhanced bioavailability of triprolidine from the transdermal TPX matrix system in rabbits; Int. J. Pharm.; 234(1-2); pp. 67-73; Mar. 2002.
Silver et al.; Transdermal nicotine and haloperidol in Tourette's disorder: a double-blind placebo-controlled study; Journal of Clinical Psychiatry; 62(9); pp. 707-714; Sep. 1, 2001.
Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.
Stocchi et al.; Motor fluctuations in levodopa treatment: clinical pharmacology; European Neurology; 36(Suppl 1); pp. 38-42; Jan. 1996.
Strong et al.; Genotype and smoking history affect risk of levodopa-induced dyskinesias in parkinson's disease; Movement Disorders; 21(5); pp. 654-659; May 1, 2006.
Thiele et al. (Ed.); Oxidants and Antioxidants in Cutaneous Biology: Current Problems in Dermatology (Book 29); S. Karger; 196 pgs.; Feb. 2001.
Togasaki et al.; Dyskinesias in normal squirrel monkeys induced by nomifensine and levodopa; Neuropharmacology; 48(3); pp. 398-405; Mar. 31, 2005.
Togasaki et al.; Levodopa induces dyskinesias in normal squirrel monkeys; Annals of Neurology; 50(2); pp. 254-257; Aug. 1, 2001.
Togasaki et al.; The Webcam system: A simple, automated, computer-based video system for quantitative measurement of movement of nonhuman primates; Journal of Neuroscience Methods; 145(1); pp. 159-166; Jun. 30, 2005.
Tolosa et al.; Antagonism by piperidine of levodopa effects in Parkinson disease; Neurology; 27(9); pp. 875-877; Sep. 1, 1977.
United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.
U.S. Department of Health and Human Services, Food and Drug Administration, Center for Drug Evaluation and Research (CDER); Guidance for industry: Abuse-deterrent opioids-Evaluation and labeling; 24 pages; retrieved from the internet (http://www.fda.gov/downloads/drugs/guidancecomplainceregulatoryinformation/guidances/ucm344743.pdf); Jan. 2013.
Vieregge et al.; Transdermal nicotine in PD: A randomized, double-blind, placebo-controlled study; Neurology; 57(6); pp. 1032-1035; Sep. 25, 2001.
Villafane et al.; Long-term nicotine administration can improve Parkinson's disease: report of a case after three years of treatment; Revista Neurologica Argentina; 27(2); pp. 95-97; (year of pub. sufficiently earlier than effective US filing date and any foreign priority date) 2002.
Warburton et al.; Facilitation of learning and state dependency with nicotine; Psychoparmacology; 89(1); pp. 55-59; May 1, 1986.
Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.
Wesnes et al.; Effects of scopolamine and nicotine on human rapid information processing performance; Psychoparmacology; 82(3); pp. 147-150; Sep. 1, 1984.
Westman et al.; Oral nicotine solution for smoking cessation: a pilot tolerability study; Nicotine and Tobacco Research; 3(4); pp. 391-396; Nov. 1, 2001.
Wille et al.; Cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.

(56) References Cited

OTHER PUBLICATIONS

Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.

Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.

Youan; Chronopharmaceutics: gimmick or clinically relevant approach to drug delivery?; J Cont Rel; 98(3); pp. 337-353; Aug. 2004.

Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.

Zubieta et al.; Placebo effects mediated by endogenous opioid activity on mu-opioid receptors; 25(34); pp. 7754-7762; Aug. 24, 2005.

Darmour et al.; U.S. Appl. No. 15/551,178 entitled "Craving input and support system," filed Aug. 15, 2017.

Darmour et al.; U.S. Appl. No. 16/115,415 entitled "Craving input and support system," filed Aug. 28, 2018.

DiPierro et al., U.S. Appl. No. 16/165,720 entitled "Optimized bio-synchronous bioactive agent delivery system," Oct. 19, 2018.

\* cited by examiner

FIG. 5

| Parameter | Nicotine (N=35) | PBO (N=27) |
|---|---|---|
| PD Duration (years) | 11.2 (4.7) | 11.1 (5.6) |
| Time Since Start of Levodopa (years) | 9.6 (4.7) | 10.2 (5.4) |
| Time Since Onset of LIDS (years) | 5.3 (3.2) | 5.2 (4.5) |
| UPDRS Total (Parts II+III+IV) | 43.5 (14.0) | 38.3 (11.7) |
| UPDRS Part III | 20.0 (8.8) | 16.9 (8.3) |
| UDPRS Part IV | 10.5 (2.8) | 9.9 (2.8) |
| UPDRS Q32+33 | 4.8 (0.9) | 4.6 (0.8) |
| UDysRS Total | 51.7 (5.4) | 48.1 (15.1) |
| UDysRS Part 1B | 20.5 (7.7) | 18.7 (7.3) |
| UDysRS Part 2B | 5.9 (3.9) | 4.5 (4.0) |
| UDysRS Part 3 | 13.5 (5.4) | 12.7 (4.9) |
| UDysRS Part 4 | 7.8 (2.9) | 7.6 (2.4) |
| LF-ADL | 11.8 (3.3) | 10.9 (3.6) |

COMPOSITIONS AND METHODS FOR TREATMENT OF SYMPTOMS IN PARKINSON'S DISEASE PATIENTS

This application is a continuation of co-pending U.S. patent application Ser. No. 14/838,208, filed Aug. 27, 2015, which is a continuation of U.S. patent application Ser. No. 13/541,333, filed Jul. 3, 2012, now abandoned, which claims priority from U.S. Provisional Application No. 61/504,974, filed Jul. 6, 2011, the entire contents of each of which are hereby incorporated by reference in their entirety.

BACKGROUND OF THE INVENTION

Parkinson's disease (also known as Parkinson disease, Parkinson's, idiopathic parkinsonism, primary parkinsonism, PD, or paralysis agitans) is a degenerative disorder of the central nervous system. It results from the death of dopamine-containing cells in the substantia nigra, a region of the midbrain; the cause of cell-death is unknown. Early in the course of the disease, the most obvious symptoms are movement- and balance-related, including shaking, rigidity, slowness of movement and difficulty with walking and gait. The main motor symptoms are collectively called parkinsonism, or a "parkinsonian syndrome". The pathology of the disease is characterized by the accumulation of a protein called alpha-synuclein into inclusions called Lewy bodies in neurons, and from insufficient formation and activity of dopamine produced in certain neurons of parts of the midbrain.

Modern treatments try to manage the early motor symptoms of the disease, mainly through the use of levodopa and dopamine agonists. As the disease progresses and dopamine neurons continue to be lost, a point eventually arrives at which these drugs become ineffective at treating the symptoms and at the same time produce a complication called dyskinesia, marked by involuntary writhing movements. Therefore, there is a need in the art to treat motor symptoms in subjects with Parkinson's Disease, including symptoms of Parkinson's Disease as well as symptoms indirectly associated with Parkinson's Disease, such as those arising as side effects of treatment.

SUMMARY OF THE INVENTION

In some aspects, the present disclosure provides for a pulsatile or extended release dosage form for once or twice-daily administration, said form comprising a capsule or tablet comprising an effective amount of nicotine for treatment of symptoms of Parkinson's Disease or symptoms associated with dopaminergic treatment of Parkinson's Disease, wherein said capsule or tablet exhibits extended or pulsatile release of said nicotine. In various aspects, said pulsatile release comprises a first and second release peak, wherein said first release peak occurs within about two hours of administration to a patient, and said second release peak occurs between about two and about twelve hours of administration to a patient. In various aspects, said extended release comprises an efficacious plasma concentration of nicotine or a metabolite thereof within one hour from administration for a duration of at least six hours and further wherein said capsule or tablet achieves a peak plasma concentration of nicotine or a metabolite thereof at least two hours after administration.

Dosage forms according to the invention include capsules and tablets. In various embodiments, a capsule comprises a powder comprising nicotine for providing said first release peak upon administration to a patient, and said capsule further comprises beads comprising nicotine for providing said second release peak upon administration to a patient. In various embodiments, the capsule or tablet comprises a water-swellable polymeric matrix. For example, in various embodiments, the dosage form swells with water upon administration to the subject's upper gastrointestinal tract such that the swellable dosage form promotes gastric retention in the stomach.

In various aspects, the present disclosure provides a delayed release dosage form for once or twice-daily administration, said form comprising a liquid filled capsule comprising an effective amount of nicotine for treatment of symptoms of Parkinson's Disease or symptoms associated with dopaminergic treatment of Parkinson's Disease, wherein said capsule comprises a hard gelatin outer surface.

In various aspects, the present disclosure provides a method of treating gait and balance problems in a subject, comprising administering an oral composition comprising nicotine, wherein the gait and balance problems are direct symptoms of Parkinson's Disease.

In some aspects, the present disclosure provides for a delayed release dosage form for once or twice-daily administration, comprising a tablet core comprising an effective amount of nicotine, the tablet core being surrounded by an outer surface, and an enteric coating completely covering the outer surface of the tablet core, the coating comprising an enteric polymer.

In some aspects, the present disclosure provides for a delayed release dosage form for treatment of gait and balance problems in Parkinson's Disease, comprising a tablet core comprising an effective amount of nicotine, the tablet core being surrounded by an outer surface, and an enteric coating completely covering the outer surface of the tablet core, the coating comprising an enteric polymer.

In some embodiments, the enteric coating dispenses the nicotine in a metered fashion when the pH is above about 5.0. The nicotine can be present at less than about 10 mg. The nicotine can be present at about 6 mg. The nicotine can be present at about 3 mg.

In some embodiments, the enteric polymer is selected from the group consisting of: a methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate. In some embodiments, a gastric retained swellable, sustained-release tablet has a matrix comprising polyethylene oxide and hydroxypropylmethylcellulose.

In some embodiments, the dosage form is capable of being administered so that one or more metabolites of said nicotine achieves a plasma level of about 1 to about 500 ng/ml within four hours of administration.

In other aspects, the present disclosure provides for a method of treating gait and balance problems in a subject, comprising administering an oral composition comprising nicotine, wherein the gait and balance problems are direct symptoms of Parkinson's Disease.

In some embodiments, the oral composition comprises an enteric coating. In some embodiments, the enteric coating dispenses the nicotine in a metered fashion when the pH is above about 5.0. The nicotine can be present at less than about 10 mg. The nicotine can be present at about 6 mg. The nicotine can be present at about 3 mg. In some embodiments, the enteric polymer is selected from the group consisting of: a methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate.

In some embodiments, the dosage form is capable of being administered so that one or more metabolites of said nicotine achieves a plasma level of about 1 to about 500 ng/ml within four hours of administration.

In various embodiments, the dosage form of nicotine further comprises a dopaminergic agent such as levodopa and/or carbidopa. In various embodiments, a dopaminergic agent is excluded. For example, in various embodiments, the dosage form and/or method of treatment does not include levodopa and/or carbidopa.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows baseline demographics of subjects of a phase II clinical trial of nicotine.

DETAILED DESCRIPTION OF THE INVENTION

Figure 1:
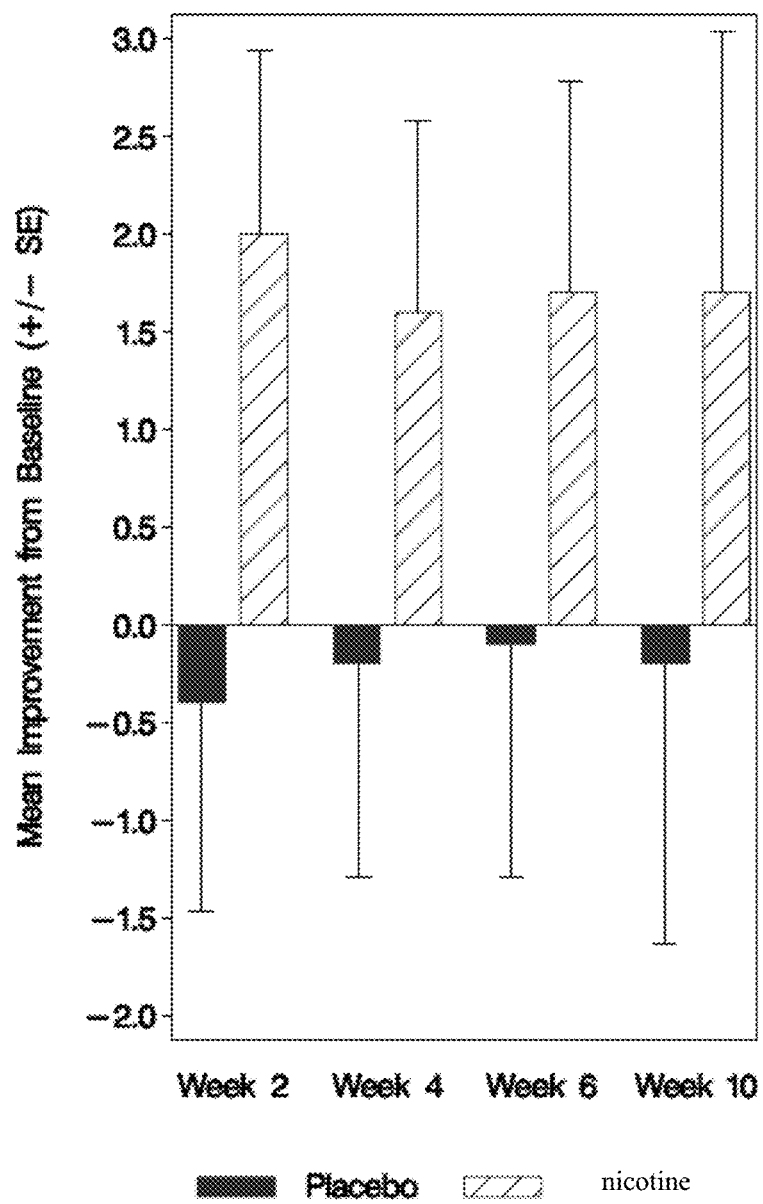
FIG. 1 shows improvement in Unified Parkinson's Disease Rating Scale Part III score for nicotine compared to placebo.

In some aspects, the present disclosure provides for an extended release or pulsatile release dosage form for once or twice-daily administration, said form comprising a capsule or tablet comprising an effective amount of nicotine for treatment of symptoms of Parkinson's Disease or symptoms associated with dopaminergic treatment of Parkinson's Disease, wherein said capsule or tablet exhibits extended or pulsatile release of said nicotine. In various aspects, said pulsatile release comprises a first and second release peak, wherein said first release peak occurs within about two hours of administration to a patient, and said second release peak occurs between about two and about twelve hours of administration to a patient. In various aspects, said extended release capsule or tablet achieves an efficacious plasma concentration of nicotine or a metabolite thereof within one hour from administration for a duration of at least six hours and further wherein said capsule or tablet achieves a peak plasma concentration of nicotine or a metabolite thereof at least about two hours after administration.

Dosage forms according to the invention include capsules and tablets. In various embodiments, said capsule comprises a powder comprising nicotine for providing said first release peak upon administration to a patient, and said capsule further comprises beads comprising nicotine for providing said second release peak upon administration to a patient. Beads are selected from the group consisting of enteric-coated beads, erodible-matrix beads, wax-coated beads, ethylcellulose-coated beads, silicone elastomer coated beads, and combinations thereof. In various embodiments, said capsule comprises a water-swellable matrix to provide a gastroretentive formulation with extended release. A water-swellable matrix may comprise polyethylene oxide, hydroxypropylmethylcellulose, and combinations thereof.

In various embodiments, the dosage form comprises a water-swellable polymeric membrane. Preferably, the water-swellable polymeric membrane ruptures following administration to a patient.

In various embodiments, the dosage form is a tablet. Tablets comprising a coating and a core, wherein said coating comprises nicotine for the first release peak, and said core comprises nicotine for the second release peak, are encompassed. In various embodiments, the coating is selected from an enteric coating, an erodible-matrix coating, a wax coating, an ethylcellulose coating, a silicone elastomer coating, and combinations thereof. In various embodiments, the tablet provides for extended release.

Also disclosed herein is a delayed release dosage form for once or twice-daily administration, said form comprising a liquid filled capsule comprising an effective amount of nicotine for treatment of symptoms of Parkinson's Disease or symptoms associated with dopaminergic treatment of Parkinson's Disease, wherein said capsule comprises a hard gelatin outer surface.

In various embodiments, nicotine is present at less than about 10 mg, or present at about 6 mg, or present at about 4 mg, or present at about 3 mg. In various embodiments, a first pulse of about 1-2 mg nicotine is released in a first release, and a second pulse of about 2-3 mg nicotine is released in a second release.

In various embodiments, the dosage form is capable of being administered so that one or more metabolites of said nicotine achieves a plasma level of about 1 to about 500 ng/ml within four hours of administration.

Also described herein is a method of treating gait and balance problems in a subject, comprising administering an oral composition comprising nicotine, wherein the gait and balance problems are symptoms of Parkinson's Disease. In various embodiments, nicotine is present at less than about 10 mg, or present at about 6 mg, or present at about 4 mg, or present at about 3 mg. In various embodiments, a first pulse of about 1-2 mg nicotine is released in a first release, and a second pulse of about 2-3 mg nicotine is released in a second release. In various embodiments, once-daily administration is provided with an effective serum concentration of nicotine or a metabolite thereof being reached within an hour and being maintained for greater than six hours from administration.

In some embodiments, the present disclosure provides for a delayed release dosage form for once or twice-daily administration, comprising a tablet core comprising an effective amount of nicotine, the tablet core being surrounded by an outer surface, and an enteric coating completely covering the outer surface of the tablet core, the coating comprising an enteric polymer. A delayed release dosage form of the present disclosure may comprise an oral formulation of nicotine.

In other embodiments, the present disclosure provides for a dosage form for treatment of gait and balance problems in Parkinson's Disease (PD), comprising a tablet core comprising an effective amount of nicotine, the tablet core being surrounded by an outer surface, and an enteric coating completely covering the outer surface of the tablet core, the coating comprising an enteric polymer. In various embodiments for direct treatment of symptoms of Parkinson's Disease, a dopaminergic agent may be excluded from the method of treatment. In various embodiments, levodopa and/or carbidopa are excluded from the method of treatment.

In some embodiments, the invention provides compositions and methods utilizing nicotine to reduce, alleviate, or eliminate symptoms of Parkinson's Disease or symptoms associated with Parkinson's Disease, e.g., a side effect associated with dopaminergic agent treatment. In some embodiments, the invention provides compositions and methods utilizing nicotine, e.g., to reduce or eliminate a side effect associated with dopaminergic agent treatment. In some embodiments, the nicotine reduces or eliminates a side effect associated with dopaminergic agent treatment. Dopaminergic agents include a dopamine precursor or a dopamine receptor agonist. Examples of dopaminergic agents include levodopa, bromocriptine, pergolide, pramipexole, cabergoline, ropinorole, apomorphine or a combination thereof.

As used herein, the term "pH independent release" refers to a rate of release of a drug from a dosage form that does not change when the pH of the environment in which the dosage form is found is changed, e.g., from an acidic pH to a higher pH. The term "pH dependent release" refers to a rate of release of a drug from a dosage form that changes when the pH of the environment in which the dosage form is found is changed from, e.g., an acidic pH to a higher pH.

As used herein, the term "zero-order release" refers to a uniform or nearly uniform rate of release of a drug from a dosage form during a given period of release, a rate of release that is independent of the concentration of drug in the dosage form. A dosage form with a zero-order release profile is referred to herein as a "zero-order dosage form." Any zero-order dosage form has the advantage of providing maximum therapeutic value while minimizing side effects.

The term "oral administration," as used herein, refers a form of delivery of a dosage form of a drug to a subject, wherein the dosage form is placed in the mouth of the subject and swallowed.

The term "orally deliverable" herein means suitable for oral administration.

The term "enteric coating," as used herein, refers to a tablet coating that is resistant to gastric juice, and which dissolves after a dosage form with the enteric coating passes out of the stomach, after oral administration to a subject.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

The term "excipient," as used herein, means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, lubricants, glidants, substances added to mask or counteract a disagreeable taste or odor, flavors, dyes, fragrances, and substances added to improve appearance of the composition.

A pH-dependent delayed release characteristic of one embodiment of the dosage form of the present disclosure result from an enteric coating. Once the dosage form leaves the highly acidic environment of the stomach and enters the higher pH of the lower gastrointestinal tract, the enteric coating dissolves, and the tablet core matrix controls the rate of release of drug remaining therein. The enteric coating preferably dissolves at a pH of at least about 5. In some embodiments, the enteric coating dissolves at a pH of at least about 5.5, 6.0, 6.5, 7.0, 7.5, or 8.0.

In some embodiments, the dosage form comprises an enteric coating and nicotine, wherein the enteric coating dispenses the nicotine in a metered fashion when said pH is above about 5.0. In some embodiments, the dosage form comprises an enteric coating and nicotine, wherein the enteric coating dispenses the nicotine in a metered fashion when said pH is above about 5.5, 6.0, 6.5, 7.0, 7.5, or 8.0.

In some embodiments, in addition to a pH-dependent release rate, the dosage form of the present invention described has a controlled release rate, e.g., a zero-order release rate through changes in pH, such as occur when the dosage form passes from the stomach to the upper intestines of a subject after oral administration thereto. In the case of a human being the average pH of the fluids in a stomach is about pH 1.1, while the average pH of the upper intestinal tract is about pH 5 to about 7.

In some embodiments, an enteric coating is combined with a pore former to effect a pH-independent extended release. A pore former can allow a limited amount of environmental fluids to reach the tablet core in the upper gastrointestinal (GI) tract, including the stomach, thereby permitting a limited amount of drug to be released into the subject at that stage after oral administration. In embodiments containing pore forming agents, the drug in the tablet core diffuses out of the tablet and into the environment surrounding the tablet through channels formed initially through pore forming agents in the enteric coating, and later, after the enteric coating has dissolved, through channels formed in the matrix itself.

In some cases, an enteric coating can be used to reduce the burst effect associated with matrix tablets. This effect is thought to be related to the size of the surface area of a tablet, and to be caused by the amount of drug located on or near the surface of the tablet. This effect can be minimized through the coating of a tablet core matrix with an enteric coating with pore-former distributed therein, as described above. For this embodiment of the invention, the solubility of the drug in the tablet core need be pH dependent. It is contemplated that any drug could be used in this embodiment of the invention, provided its solubility characteristics allow for containment within and release from the matrix. The enteric coating with pore former effectively minimizes the surface area of the tablet that is initially exposed to solution in the GI tract and thus limits the amount of drug that is initially released. The coating composition, in terms of ratio of enteric to pore-former, could be changed to dictate how much the burst is minimized and therefore the release rate of the drug. A pH-sensitive enteric coating dissolves when the tablet enters the intestine and allows the core to take over the control of the tablet release.

The dosage form of the present invention can delay the period of drug release compared to uncoated tablet cores having the same composition as the tablet cores of the present dosage forms. The drug in the coated tablet cores of the present invention delay release of the drug into a subject by at least about 30 minutes, 1 hour, 1.5 hours, 2 hours, 2.5 hours, 3 hours, 4 hours, 5 hours, 6 hours, 7 hours, or 8 hours after oral administration. A dosage form that provides delayed drug release as described herein can be formulated for once or twice-daily administration.

The dosage form of the present invention can extend the period of drug release compared to uncoated tablet cores having the same composition as the tablet cores of the present dosage forms. The drug in the coated tablet cores of the present invention preferably continue to release the drug into a subject to at least 10 hours, more preferably to at least 12 hours, even more preferably to at least 14 hours, and most preferably to at least 16 hours after oral administration. A dosage form that provides continuous drug release over about 10, 11, 12, 13, or 14 hours can be formulated for once or twice-daily administration, thereby allowing continuous delivery of a drug over a 24-hour period.

In various embodiments, the release profile is a pulsatile release. For example, in various embodiments, an immediate release of nicotine is followed by an extended or delayed release of nicotine.

The terms "tablet core," "matrix," and "tablet core matrix" refer to a compressed tablet prior to coating. No specialized geometry of the tablet core is necessary in the present invention. The tablet core may be in any shape known in the pharmaceutical industry and suitable for drug delivery, such as in spherical, cylindrical, or conical shape. In the case of cylindrical shape, it generally has flat, convex, or concave surfaces. The tablet core of the dosage form of the present invention can comprise a matrix of a drug and a water soluble polymer, suitable for sustained or controlled release following exit of the tablet from the acidic environment of the stomach and dissolution of the coating upon entry into the higher pH environment of the intestine.

The tablet core is prepared by conventional dry granulation methods without using a solvent. The enteric coating is applied using a conventional process known in the art. The coated tablets of the present invention have a dual advantage in allowing ease of manufacture and affording medicament release in a substantially linear fashion over an extended period of time.

In some embodiments, the dosage form comprises an enteric coating comprising an enteric polymer. Suitable enteric polymers include, but are not limited to, methacrylic acid/methacrylic acid ester copolymer, a methacrylic acid/ acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate.

Enteric polymers suitable for use in the present invention include, but are not limited to polyacrylate copolymers such as methacrylic acid/methacrylic acid ester copolymers or methacrylic acid/acrylic acid ester copolymers, such as USP/NF, Types A, B, or C, which are available from Rohm GmbH under the brand name Eudragit™; cellulose derivatives, such as cellulose acetate phthalate, hydroxypropyl mefhylcellulose pthalate, hydroxypropyl methyl cellulose acetate succinate, and cellulose acetate trimellitate; and polyvinyl acetate phthalate, such as is available from Colorcon, under the brand name SURETERIC®, and the like. In some embodiments, the enteric polymer is a polyvinyl acetate phtalate.

Suitable water soluble pore-forming agents for use in the enteric coating in the dosage forms of the present invention include, but are not limited to, povidone K 30, polyvinyl alcohol, cellulose derivatives such as hydroxypropyl cellulose, hydroxypropyl methyl cellulose, methyl cellulose or sodium carboxymefhylcellulose; sucrose; xylitol, sorbitol, mannitol, maltose, xylose, glucose, potassium chloride, sodium chloride, polysorbate 80, polyethylene glycol, propylene glycol, sodium citrate, or combinations of any of the above. The pore-forming agent preferably comprises hydroxypropyl methyl cellulose.

The composition of the enteric coating is preferably designed to ensure adherence of the coating to the tablet core. Methods for selection of coating compositions that adhere to compressed tablets are known. See, for example, Pharmaceutical Dosage Forms: Tablets, 2nd ed., vol. 1, Lieberman et al., ed. (Marcel Dekker, Inc.; New York, N.Y.; 1989), pp. 266-271, incorporated herein by reference. Additionally, the cores can be subcoated prior to coating with an enteric coating. The subcoat can function; to provide insure that pores in the core are filled in prior to coating with an enteric coat, (insure against coating failure). The sub coat can consist of any film forming formulation examples include Opadry (Colorcon), Opadry II (Colorcon), AMT (Colorcon) and HPMC.

The enteric coating can be about 3% to about 10% by weight of the dosage form of the present invention. In some cases, the enteric coating can be about 4%, 5%, 6%, 7%, 8%, 9%, 10%, 11%, 12%, 13%, 14%, 15%, 16%, 17%, 18%, 19%, or 20% by weight of the dosage form of the present invention.

In some embodiments, the tablet core of a dosage form of the invention comprises at least one hydrophilic polymer. Suitable hydrophilic polymers include, but are not limited to, hydroxypropyl methylcellulose (hereinafter, "HPMC"), hydroxypropylcellulose, or other water soluble or swellable polymers such as sodium carboxymethyl cellulose, xanthan gum, acacia, tragacanth gum, guar gum, karaya gum, alginates, gelatin, and albumin. The hydrophilic polymers can be present in amounts ranging from about 5% to about 95% by weight of the system. In some embodiments, the hydrophilic polymers are selected from the group consisting of cellulose ethers, such as hydroxypropylmethylcellulose, hydroxypropylcellulose, methylcellulose, and mixtures thereof.

Where a given salt form of a drug is too soluble to provide desired extended release characteristics using a dosage form of the present invention, it may be preferred to use a less soluble form, such as a crystalline form, of the same drug in the dosage form.

The amount of drug in a given dosage form can be selected to accommodate the desired frequency of administration used to achieve a specified daily dosage. The amount of the unit dosage form of the composition that is administered and the dosage regimen for treating the condition or disorder will depend on a variety of factors, including the age, weight, sex and medical condition of the subject, the severity of the condition or disorder, the route and frequency of administration, and the particular drug selected, and thus may vary widely. One or more dosage forms can be administered up to about 6 times a day. In some cases, a dosage form is formulated for once or twice daily administration. However, the dosage forms of the present invention release at a delayed and/or extended rate, making it possible to provide the desired therapeutic efficacy by administration once-a-day or twice-a-day.

Dosage forms of the present invention may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, an agent (e.g., a therapeutic drug or a candidate drug) is formulated as a lyophilizate using appropriate excipient solutions (e.g., sucrose) as diluents. Diluents can be incorporated into the tablet core of a dosage form.

Dosage forms of the invention, preferably the tablet core matrix, optionally comprise one or more pharmaceutically acceptable diluents as excipients. Non-limiting examples of suitable diluents include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of a- and amorphous cellulose (e.g., Rexcel™) and powdered cellulose; calcium carbonate; glycine; bentonite; polyvinylpyrrolidone; and the like. Such diluents, if present, constitute in total about 5% to about 99%. In some embodiments, such diluents constitute in total about 10% to about 85%, or about 10% to about 80%, of the total weight of the composition.

In another embodiment of the invention, the gastric retained dosage form of nicotine is an extended release oral drug dosage form for releasing nicotine into the stomach, duodenum and small intestine of a patient, and comprises: a single or a plurality of solid particles consisting of nicotine or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii) gradually the nicotine diffuses or the polymer erodes over a time period of hours, where the diffusion or erosion commences upon contact with the gastric fluid; and (iii) releases nicotine to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107, and U.S. Pat. No. 8,192,756, the contents of each of which are incorporated by reference in their entirety.

In yet another embodiment, a bi-layer tablet releases nicotine to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of polyethylene oxide) and hydroxypropylmethylcellulose. Further details may be found in Gusler, et al. "Optimal Polymer Mixtures for Gastric Retentive Tablets," granted as U.S. Pat. No. 6,723,340, the disclosure of which is incorporated herein by reference.

Pharmaceutically acceptable carriers for therapeutic use are well known in the pharmaceutical art, and are described, for example, in Remingtons Pharmaceutical Sciences. Mack Publishing Co. (A.R. Gennaro edit. 1985). For example, sterile saline and phosphate-buffered saline at physiological pH may be used. Preservatives, stabilizers, dyes and other ancillary agents may be provided in the pharmaceutical composition. For example, sodium benzoate, sorbic acid and esters of p-hydroxybenzoic acid may be added as preservatives. In addition, antioxidants and suspending agents may be used. Id. "Pharmaceutically acceptable salt" refers to salts of drug compounds derived from the combination of such compounds and an organic or inorganic acid (acid addition salts) or an organic or inorganic base (base addition salts). The agents, including drugs, contemplated for use herein may be used in either the free base or salt forms, with both forms being considered as being within the scope of the certain present invention embodiments.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, trisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose, microcrystalline cellulose, and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymefhacrylates; hydroxypropylmethylcellulose; hydroxypropylcellulose (e.g., Klucel™); and ethylcellulose (e.g., Ethocel™). Such binding agents and/or adhesives, if present, can constitute in total about 0.5% to about 25%, about 0.75% to about 15%, or about 1% to about 10%, of the total weight of the composition.

In some embodiments, microcrystalline cellulose is a particularly preferred binder, because of its known chemical compatibility with that particular drug. The use of extragranular microcrystalline cellulose (that is, microcrystalline cellulose added to a wet granulated composition after a drying step) can also be used to improve hardness (for tablets) and/or disintegration time. Microcrystalline cellulose included in dry granulation similarly improves hardness of a tablet core.

Compositions of the invention optionally comprise one or more pharmaceutically acceptable lubricants (including anti-adherents and/or glidants) as excipients. Suitable lubricants include, either individually or in combination, glyceryl behenate (e.g., Compritol™ 888); stearic acid and salts thereof, including magnesium, calcium and sodium stearates; hydrogenated vegetable oils (e.g., Sterolex™); colloidal silica; talc; waxes; boric acid; sodium benzoate; sodium acetate; sodium fumarate; sodium chloride; DLleucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. In some embodiments, magnesium stearate is a lubricant used to reduce friction between the equipment and granulated mixture during compression of tablet formulations.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or nonionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof. Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkylphenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose monolaurate, sucrose monopalmitate, PEG 10-100 nonyl phenol series, PEG 15-100 octyl phenol series, and poloxamers. Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition. Other excipients such as colorants, flavors and sweeteners are known in the pharmaceutical art and can be used in compositions of the present invention.

In some embodiments, the dosage form of the present disclosure comprises: a tablet core comprising nicotine bitartrate dehydrate, magnesium stearate, and microcrystalline cellulose. In some embodiments, the dosage form comprises: a tablet core comprising nicotine in a water soluble polymer matrix; and an enteric coating comprising an enteric polymer and, optionally, a pore-former; wherein, the tablet core or the enteric coating or both include at least one excipient. The dosage form comprises at least one excipient preferably selected from the group consisting of pharmaceutically acceptable diluents, binding agents and lubricants. In some cases, a dosage form comprises at least one excipient selected from the group consisting of lactose (e.g., lactose monohydrate), polyvinylpyrrolidone, magnesium stearate and microcrystalline cellulose.

Standard methods of production are suitably used to produce the dosage forms of the present invention. Dry mixing of intragranular ingredients, followed by granulation, and dry mixing of intragranular ingredients with extragranular ingredients are standard techniques used in the industry. See, for example, Chapter 4 ("Compressed Tablets by Direct Compression," by Ralph F. Shangraw) of Pharmaceutical Dosage Forms: Tablets, vol. 1, 2 ed., Lieberman et al. ed., Marcel Dekker, Inc. pub. (1989), pp. 195-246. The enteric coating is suitably applied using any standard coating technique, such as the techniques described in Chapter 5 ("Compression-Coated and Layer Tablets", by William C. Gunsel et al.), of the same volume.

The present invention is also directed to a method of making the dosage forms of the present invention. In the preferred method, each of the intragranular ingredients is preferably screened or provided in pre-screened form before being dry mixed. If the intragranular ingredients have flow characteristics that make it impracticable to feed the ingredients directly into a tablet press, the ingredients can be granulated prior to compression, for example, by being run through a roller compactor to achieve a suitable ribbon.

When microcrystalline cellulose is included as an excipient in the tablet core, it is preferably included as both an intragranular and as an extragranular ingredient, and added to the other intragranular and extragranular ingredients after each set of ingredients has been mixed, separately. The microcrystalline cellulose is preferably provided pre-screened for particle size prior to addition to the other ingredients. Microcrystalline Cellulose NF Med Powder is an example of one such suitable pre-screened microcrystalline cellulose powder suitable for use in the tablet cores of the present invention.

Once the intragranular ingredients are mixed with all the extragranular ingredients, a compressed tablet is produced therefrom, using any suitable tablet press. Any standard tablet press that does not compress the tablet so far as to damage the water soluble matrix or so compress the tablet that water cannot enter the matrix and solubilize the drug contained therein. The compressed tablets are then completely coated with the enteric coating, comprising an enteric polymer and a pore-former, using any standard coating technique. The enteric coating can be applied in the form of a thin layer.

In some embodiments, the invention includes a multilayer tablet comprising an immediate release layer and a sustained release layer. In some embodiments, the immediate release layer comprises nicotine or a metabolite. In some embodiments, the sustained release layer comprises nicotine or a metabolite. In some embodiments, the immediate release layer and sustained release layer both comprise nicotine or a metabolite.

Nicotine

Nicotine may be isolated and purified from nature or synthetically produced in any manner. This term "nicotine" is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23. The systematic name of nicotine is 3-[(2S)-1-methylpyrrolidin-2-yl]pyridine and its structure is:

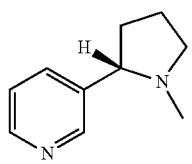

Unless specifically indicated otherwise, the term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof. A number of useful derivatives of nicotine are disclosed within the Physician's Desk Reference (most recent edition) as well as Harrison's Principles of Internal Medicine. Methods for production of nicotine derivatives and analogues are well known in the art. See, e.g., U.S. Pat. Nos. 4,590,278; 4,321,387; 4,452,984; 4,442,292; and 4,332,945.

The compounds of the present invention may have asymmetric carbon atoms. All isomers, including diastereomeric mixtures such as racemic mixtures and pure enantiomers are considered as part of the invention.

Without being limited to any one theory, one mechanism of action can be that after a prolong exposure to nicotinic receptor agonist nicotinic receptors become desensitized and the nicotinic receptor agonists start working as nicotinic receptor antagonists. In some embodiments, the nicotinic receptor agonists work as antagonists to reduce or eliminate a side effect induced by a dopaminergic agent.

In some embodiments, the invention provides a composition for administration of nicotine to an animal. In some embodiments, the invention provides a composition for administration of nicotine to an animal to reduce a side effect of a dopaminergic agent, e.g., for the oral delivery of nicotine, that contain at least about 1, 5, 10, 20, 30, 40, 50, 60, 70, 80, 90, 95, 99, 99.5, 99.9, or 99.99% nicotine. In some embodiments, the invention provides a composition for the oral delivery of nicotine that contains no more than about 2, 5, 10, 20, 30, 40, 50, 60, 70, 80, 90, 95, 99, 99.5, 99.9, 99.99, or 100% nicotine. In some embodiments, the invention provides a composition that contains about 1-100% nicotine, or about 10-100% nicotine, or about 20-100% nicotine, or about 50-100% nicotine, or about 80%-100% nicotine, or about 90-100% nicotine, or about 95-100% nicotine, or about 99-100% nicotine. In some embodiments, the invention provides a composition that contains about 1-90% nicotine, or about 10-90% nicotine, or about 20-90% nicotine, or about 50-90% nicotine, or about 80-90% nicotine. In some embodiments, the invention provides a composition that contains about 1-75% nicotine, or about 10-75% nicotine, or about 20-75% nicotine, or about 50-75% nicotine. In some embodiments, the invention provides a composition that contains about 1-50% nicotine, or about 10-50% nicotine, or about 20-50% nicotine, or about 30-50% nicotine, or about 40-50% nicotine. In some embodiments, the invention provides a composition that contains about 1-40% nicotine, or about 10-40% nicotine, or about 20-40% nicotine, or about 30-40% nicotine. In some embodiments, the invention provides a composition that contains about 1-30% nicotine, or about 10-30% nicotine, or about 20-30% nicotine. In some embodiments, the invention provides a composition that contains about 1-20% nicotine, or about 10-20% nicotine. In some embodiments, the invention provides a composition that contains about 1-10% nicotine. In some embodiments, the invention provides a composition that contains about 1, 2, 5, 10, 20, 30, 40, 50, 60, 70, 80, 90, 95, 96, 97, 98, or 99% nicotine.

In some embodiments, the a concentration of nicotine is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, a concentration of nicotine is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25% 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25% 7%, 6.75%, 6.50%, 6.25% 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, a concentration of nicotine is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, a concentration of nicotine is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of nicotine is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of nicotine is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Nicotinic Receptor Modulators

In one aspect, the invention provides compositions and methods utilizing a nicotinic receptor modulator, e.g., to reduce or eliminate a side effect associated with dopaminergic agent treatment. A nicotinic receptor modulator can be an agonist or it can be an antagonist.

The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that enhance a biological activity of the target polypeptide by interacting with other members of the signal transduction pathway of which the target polypeptide is a member are also specifically included within this definition. Agonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

In some embodiments, the nicotinic receptor modulator modulates a nicotinic receptor in the brain. In some embodiments, the nicotinic receptor modulator modulates a nicotinic receptor in the striatum or substantia nigra. In some embodiments, the nicotinic receptor modulator modulates a nicotinic receptor comprising at least one α subunit or a nicotinic receptor containing at least one α subunit and at least one β subunit. In some embodiments, the α subunit is selected from the group consisting of α2, α3, α4, α5, α6, α7, α8, α9, and α10 and the β subunit is selected from the group consisting of β2, β3 and β4. In some embodiments, the nicotinic receptor modulator modulates a nicotinic receptor comprising subunits selected from the group consisting of α4β2, α6β2, α4α6β2, α4α5β2, α4α6β2β3, α6β2β3 and α4α2β2. In some embodiments, the nicotinic receptor modulator modulates a nicotinic receptor comprising at least one α subunit selected from the group consisting of α4, α6, and α7.

The nicotinic receptor agonist of the invention may be any ligand that binds to and activates the nicotinic receptor, thereby resulting in a biological response. The potential of a given substance to act as a nicotinic receptor agonist may be determined using standard in vitro binding assays and/or standard in vivo functionality tests.

Other nicotinic receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side-effects (e.g., Epidoxidine, ABT-154, ABT418, ABT-594; Abbott Laboratories (Damaj et al. (1998) J. Pharmacol Exp. Then 284:1058 65, describing several analogs of epibatidine of equal potency but with high specificity to the neuronal type of nicotinic receptors). Further nicotinic receptor agonists of interest include, but are not necessarily limited to, N-methylcarbamyl and N-methylthi-O-carbamyl esters of choline (e.g., trimethylaminoethanol) (Abood et al. (1988) Pharmacol. Biochem. Behav. 30:403 8); acetylcholine (an endogenous ligand for the nicotinic receptor); and the like.

Dopaminergic Agents

In one aspect, the invention provides compositions and methods to reduce or eliminate the effects of a dopaminergic agent. In some embodiments, the compositions and methods retain or enhance a desired effect of the dopaminergic agent, e.g., antiparkinsonian effect. The methods and compositions of the invention apply to any dopaminergic agent for which it is desired to reduce one or more side effects. In some embodiments, the compositions and methods of the invention utilize a dopamine precursor. In some embodiments, the compositions and methods of the invention utilize a dopamine agonist. In some embodiments, the dopaminergic agent is levodopa, bromocriptine, pergolide, pramipexole, cabergoline, ropinorole, apomorphine or a combination thereof. In some embodiments, the dopaminergic agent is levodopa. In some embodiments, the compositions and methods of the invention utilize one or more agents used in the art in combination with a dopamine agent treatment to achieve a therapeutic effect. For instance, in one exemplary embodiment the compositions and methods of the invention utilize levodopa in combination with an agent such as carbidopa, which blocks the conversion of levodopa to dopamine in the blood. In another exemplary embodiment, the compositions and methods of the invention utilize levodopa in combination with a COMT Inhibitor, such as entacapone. In another exemplary embodiment, the compositions and methods of the invention utilize levodopa in combination with a monoamine oxidase type B (MAO-B) inhibitor such as selegiline. In yet another exemplary embodiment, the compositions and methods of the invention utilize levodopa in combination with amantadine.

Levodopa

Levodopa, an aromatic amino acid, is a white, crystalline compound, slightly soluble in water, with a molecular weight of 197.2. It is designated L-3,4-dihydroxyphenylalanine (S)-2-amino-3-(3,4-dihydroxyphenyl)propanoic acid. Its structural formula is

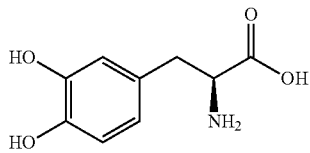 [SMILES: N[C@@H](Cc1ccc(O)c(O)c1)C(=O)O]

Levodopa is used for the treatment of Parkinson's disease. Parkinson's disease is a progressive, neurodegenerative disorder of the extrapyramidal nervous system affecting the mobility and control of the skeletal muscular system. Its characteristic features include resting tremor, rigidity, and bradykinetic movements. Current evidence indicates that symptoms of Parkinson's disease are related to depletion of dopamine in the corpus striatum. Administration of dopamine is ineffective in the treatment of Parkinson's disease apparently because it does not cross the blood-brain barrier. However, levodopa, the metabolic precursor of dopamine, does cross the bloodbrain barrier, and presumably is converted to dopamine in the brain. This is thought to be the mechanism whereby levodopa relieves symptoms of Parkinson's disease.

However, although initially very effective, long term treatment with levodopa gives rise to multiple complications. Levodopa treatment may cause nausea, vomiting, involuntary movements (e.g. dyskinesias), mental disturbances, depression, syncope, and hallucinations. The precise pathophysiological mechanisms of levodopa side effects are still enigmatic, but are thought to be due to increased brain dopamine following administration of levodopa. Previous work has shown that levodopa induced dyskinesias (LIDs) arise due to enhanced intermittent stimulation of D1, D2 and/or other dopamine receptor subtypes. This results in an imbalance in activity of the two major striatal output pathways, possibly through activation of D1 and inhibition of D2 receptors on the direct and indirect dopaminergic pathways, respectively, although there is some overlap between striatal efferents. Recent data suggest that D1 receptors, through enhanced G-protein coupling, may play a more prominent role in functional hypersensitivity associated with levodopa-induced dyskinesias, while D2 receptor activation may be more closely linked to the antiparkinsonian action of dopaminergic drugs Side Effects The principal adverse reactions of dopaminergic agent include headache, diarrhea, hypertension, nausea, vomiting, involuntary movements (e.g. dyskinesias), mental disturbances, depression, syncope, hallucinations, and abnormal renal function.

The invention provides compositions and methods utilizing nicotine or a nicotinic receptor modulator that reduces or eliminates a side effect associated with dopaminergic agent treatment. In some embodiments, the invention provides compositions and methods utilizing a nicotinic receptor modulator that reduces or eliminates dyskinesias associated with dopaminergic agent treatment. Without being limited to any theory, one possibility is that nicotinic receptor modulator exerts its effect by acting at nicotinic acetylcholine receptors (nAChR), which are expressed in the striatum. There is a dense cholinergic innervation in striatum that closely coincides with dopaminergic neurons. Under physiological conditions, these cholinergic interneurons tonically release acetylcholine, which stimulates nicotinic receptors on dopaminergic nerve terminals to release dopamine. Similarly, exogenously applied agents such as nicotine result in a release of dopamine from striatal terminals.

Methods of Treatment

In some embodiments the invention provides methods of decreasing a side effect of a dopaminergic agent in an animal, e.g. a human, that has received an amount of the dopaminergic agent sufficient to produce a side effect by administering to the animal, e.g., human, an amount of nicotine sufficient to reduce or eliminate the side effect.

The side effect may be acute or chronic. The effect may be biochemical, cellular, at the tissue level, at the organ level, at the multi-organ level, or at the level of the entire organism. The effect may manifest in one or more objective or subjective manners, any of which may be used to measure the effect. If an effect is measured objectively or subjectively (e.g., dyskinesias and the like), any suitable method for evaluation of objective or subjective effect may be used. Examples include visual and numeric scales and the like for evaluation by an individual. A further example includes sleep latency for measurement of drowsiness, or standard tests for measurement of concentration, mentation, memory, and the like. These and other methods of objective and subjective evaluation of side effects by an objective observer, the individual, or both, are well-known in the art.

In some embodiments, the invention provides a composition comprising nicotine, wherein the nicotine is present in an amount sufficient to decrease a side effect of a dopaminergic agent by a measurable amount, compared to the side effect without the nicotine, when the composition is administered to an animal. In some embodiments, a side effect of the dopaminergic agent is decreased by an average of at least about 5, 10, 15, 20, 25, 30, 35, 40, 45, 50, 55, 60, 65, 70, 75, 80, 85, 90, 95, or more than 95%, compared to the side effect without the nicotine. In some embodiments, a side effect of the dopaminergic agent is decreased by an average of at least about 5%, compared to the side effect without the nicotine. In some embodiments, a side effect of the dopaminergic agent is decreased by an average of at least about 10%, compared to the side effect without the nicotine. In some embodiments, a side effect of the dopaminergic agent is decreased by an average of at least about 15%, compared to the side effect without the nicotine. In some embodiments, a side effect of the dopaminergic agent is decreased by an average of at least about 20%, compared to the side effect without the nicotine. In some embodiments, a side effect of the dopaminergic agent is decreased by an average of at least about 30%, compared to the side effect without the nicotine. In some embodiments, a side effect is substantially eliminated compared to the side effect without the nicotine. "Substantially eliminated" as used herein encompasses no measurable or no statistically significant side effect (one or more side effects) of the dopaminergic agent, when a nicotine is administered. In some embodiments, the side effect is dyskinesias.

In some embodiments, the invention provides compositions containing a nicotinic receptor agonist, e.g., nicotine, present in an amount sufficient to decrease a side effect of a dopaminergic agent by an average of at least about 5% and to increase a therapeutic effect of the dopaminergic agent by an average of at least about 5%, when the composition is administered to an animal in combination with the dopaminergic agent, compared to the side effect and therapeutic effect without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 10%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 20% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 30%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 40%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 50%, when the composition is administered to an animal in combination with the dopaminergic agent, compared to the side effect and therapeutic effect when the dopaminergic agent is administered without the a nicotinic receptor agonist, e.g., nicotine.

In exemplary embodiments, the invention provides a composition that contains nicotine and a dopaminergic agent, such as levodopa or a dopamine agonist, where the dopaminergic agent is present in an amount sufficient to exert a therapeutic effect, and nicotine is present in an amount effective to decrease a side effect of the dopaminergic agent by a measurable amount (e.g., an average of at least about 5, 10, 15, 20, 30 or more than 30%, as described herein) and to increase the therapeutic effect of the dopaminergic agent by a measurable amount (e.g., an average of at least about 5, 10, 15, 20, 30 or more than 30%, as described herein). The side effect may be any side effect as described herein. In some embodiments, the side effect is dyskinesia.

An "average" as used herein is preferably calculated in a set of normal human subjects, this set being at least about 3 human subjects, preferably at least about 5 human subjects, preferably at least about 10 human subjects, even more preferably at least about 25 human subjects, and most preferably at least about 50 human subjects.

The term "animal" or "animal subject" as used herein includes humans as well as other mammals. The methods generally involve the administration of one or more drugs for the treatment of one or more diseases. Combinations of agents can be used to treat one disease or multiple diseases or to modulate the side-effects of one or more agents in the combination.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The methods of the invention may be used for treatments of any suitable condition where one or more dopaminergic agents are used that have side effects. Examples of conditions include, but are not limited to, Parkinson's disease, Alzheimer, dopa-responsive dystonia, cerebral palsy, postischemic contractile dysfunction, severe ovarian hyperstimulation syndrome, pediatric movement disorders and non-oliguric renal failure.

In various embodiments, the methods of treatment are directed to direct symptoms of Parkinson's Disease rather than treatment of a dopaminergic agent-induced side effect. For example, in various embodiments, the methods of treatment are directed to treatment of gait and balance deficits resulting directly from Parkinson's Disease. In various embodiments, nicotine is administered separately from any dopaminergic agent. In various embodiments, the subject undergoing treatment with nicotine is not receiving a dopaminergic agent. In various embodiments, the subject undergoing treatment with nicotine is not receiving levodopa, carbidopa, or combinations thereof.

In some embodiments, an effective amount of nicotine is administered such that the nicotine or a metabolite of the nicotine reaches a critical concentration in the bloodstream, plasma, or the tissue. In some embodiments, the nicotine is administered such that the nicotine or a metabolite of nicotine reaches a critical concentration in the bloodstream, plasma or tissue 48, 36, 24, 12, 10, 8, 6, 5, 4, 3, 2, or 1 hours following administration.

In some embodiments, the critical concentration of the nicotine or a nicotine metabolite is about 1 pg/ml to about 1 mg/ml. In some embodiments the critical concentration nicotine or nicotine metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiments, the critical concentration of the nicotine or a nicotine metabolite is about 200 ng/ml to about 420 ng/ml. In some embodiments, the critical concentration of the nicotine or a nicotine metabolite is about 1 ng/ml to about 20 ng/ml. In some embodiments, the critical concentration of the nicotine or a nicotine metabolite is about 1 ng/ml to about 5 ng/ml. In some embodiments, the critical concentration of the nicotine or a nicotine metabolite is about 20 ng/ml to about 100 ng/ml. In some embodiments, the nicotine metabolite is cotinine.

Dosing and Administration

Dosing ranges for dopaminergic agents are known in the art. It is also known in the art that due to intersubject variability in dopaminergic agents, such as levodopa, pharmacokinetics, individualization of dosing regimen is necessary for optimal therapy. For an nicotinic receptor agonist, e.g., nicotine, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of nicotine is about 1, 5, 10, 15, 20, 25, 30, 35, 40, 45, 50, 100, 200, 300, 400, 500, 600, 700, 800, 900, or 1000 mg. In some embodiments, the daily dose of nicotine is 0.9 mg. In some embodiments, the daily dose of nicotine is 1.8 mg. In some embodiments, the daily dose of nicotine is 2.4 mg. In some embodiments, the daily dose of nicotine is 3 mg. In some embodiments, the daily dose of nicotine is 6 mg. In some embodiments, the daily dose of nicotine is 7 mg. In some embodiments, the daily dose of nicotine is 8 mg. In some embodiments, the daily dose is administered in two equal parts during the day, such as about 4 mg twice daily. In some embodiments, the daily dose of nicotine is 9 mg. In some embodiments, the daily dose of nicotine is 12 mg. In some embodiments, the daily dose of nicotine is 14 mg. In some embodiments, the daily dose of nicotine is 18 mg. In some embodiments, the daily dose of nicotine is 21 mg. In some embodiments, the daily dose of nicotine is 24 mg. In some embodiments, the daily dose of nicotine is 32 mg. In some embodiments, the daily dose of nicotine is 50 mg. In some embodiments, the daily dose of nicotine is less than 93 mg. Daily dose range may depend on the form of nicotinic receptor agonist and/or factors with which the nicotinic receptor agonist is administered, as described herein.

In some embodiment the daily dose of nicotine is such that the plasma level of nicotine or a nicotine metabolite is about 1 pg/ml to about 1 mg/ml. In some embodiments the daily dose of nicotine is such that the plasma level or nicotine or nicotine metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiment, the daily dose of nicotine is such that the plasma level of nicotine or a nicotine metabolite is about 200 ng/ml to about 420 ng/ml. In some embodiment, the daily dose of nicotine is such that the plasma level of nicotine or a nicotine metabolite is about 1 ng/ml to about 20 ng/ml. In some embodiment, the daily dose of nicotine is such that the plasma level of nicotine or a nicotine metabolite is about 1 ng/ml to about 5 ng/ml. In some embodiment, the daily dose of nicotine is such that the plasma level of nicotine or a nicotine metabolite is about 20 ng/ml to about 100 ng/ml.

In some embodiments, nicotine is administered in multiple doses. Dosing may be about once, twice, three times, four times, five times, six times, or more than six times per day. Dosing may be about once a month, once every two weeks, once a week, or once every other day. In some embodiments, dosing is once or twice daily. In some embodiments the administration of nicotine continues for less than about 7 days. In another embodiment the administration continues for more than about 6, 10, 14, 28 days, two months, six months, or one year. In some cases, continuous dosing is achieved and maintained as long as necessary.

Administration of nicotine of the invention may continue as long as necessary. In some embodiments, nicotine of the invention is administered for more than 1, 2, 3, 4, 5, 6, 7, 14, 28 days or 1 year. In some embodiments, nicotine of the invention is administered for less than 28, 14, 7, 6, 5, 4, 3, 2, or 1 day. In some embodiments, nicotine of the invention is administered chronically on an ongoing basis, e.g., for the treatment of chronic effects.

In some embodiments, nicotine is orally administered using an orally disintegrating tablet. Examples of orally disintegrating tablets are known, such as disclosed in U.S. Pat. Nos. 7,282,217; 7,229,641; 6,368,625; 6,365,182; 6,221,392; and 6,024,981.

In various embodiments, nicotine is administered to yield an extended release which comprises a single peak plasma concentration of nicotine or a metabolite thereof, wherein said single peak plasma concentration occurs between about two hours and about 12 hours after administration. In various embodiments, the extended release comprises a single peak plasma concentration of nicotine or a metabolite thereof, wherein said single peak plasma concentration occurs between about six hours and about eight hours after administration. In various embodiments, the extended release achieves an efficacious plasma concentration of nicotine or a metabolite thereof within one hour from administration and achieves a duration of an efficacious plasma concentration of nicotine or a metabolite thereof for a period between about six to about 18 hours from administration. In various embodiments, the extended release achieves an efficacious plasma concentration of nicotine or a metabolite thereof within one hour from administration and achieves a duration of an efficacious plasma concentration of nicotine or a metabolite thereof for a period between about eight hours to about 14 hours from administration. In various embodiments, the extended release achieves an efficacious plasma concentration of nicotine or a metabolite thereof within one hour from administration and achieves a duration of an efficacious plasma concentration of nicotine or a metabolite thereof for a period between about ten hours to about 12 hours from administration.

Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-inwater emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

EXAMPLES

Example 1: Clinical Trial

A total of 65 patients with idiopathic PD and LIDS were enrolled in a phase II study. Major entry criteria were as follows: 1) Hoehn and Yahr Stage II-IV while in "on" state, 2) had moderately to severely disabling LIDS>25% of waking day as determined by a rating of >2 on each of Questions 32 and 33 of the Unified Parkinson's Disease Rating Scale (UPDRS), 3) be on stable doses of levodopa and other medicines for PD for >30 days, 4) have a negative screening urine test for cotinine, and 5) not be a smoker or previous smoker or regular exposure to second-hand smoke. The study consisted of 3 phases: a treatment period of 10 weeks, a 9-day drug taper period, and a 5-day follow-up period. Subjects were randomly assigned to receive either nicotine or placebo (pbo). Dosing began at 1 mg q6 hr and was escalated at 2-week intervals to 6 mg q6 hr (24 mg/day). All subjects were allowed to take ondansetron as rescue medication for the treatment of nausea and/or vomiting for the first 3 days of each dose escalation. Subjects were maintained on 24 mg/day for 4 weeks.

Safety was assessed by incidences of adverse experiences (AE), clinical laboratory tests, serum cotinine, ECG and vital signs. Impulsive symptoms were assessed using the Jay Modified Minnesota Impulsive Disorders Interview (JayMidi). Withdrawal symptoms were evaluated using the Minnesota Nicotine Withdrawal Scale (MNWS-R).

Efficacy was assessed using the UPDRS (total of Parts II+III+IV), sum of Q32+Q33, Unified Dyskiensia Rating Scale (UDysRS) total scores and subscores, Lang-Fahn Dyskinesia Activities of Daily Living Scale (LF-ADL), physician and patient ratings of improvement from baseline in dyskinesias on 7-point CGI-C and PGI-C scales, and responder analyses (subjects with >25% improvement from baseline) on UDysRS total score and LF-ADL, and % subjects with any improvement on PGI-C and CGI-C.

The safety population for all safety analyses consisted of all subjects who received at least 1 dose of nicotine or placebo. Efficacy analyses were conducted on all subjects who took at least 1 dose of study medication, had a baseline and at least one post-baseline assessment.

A total of 65 patients were randomized to treatment (nicotine=35, pbo=30) and a total of 63 patients completed the trial; medication compliance in each group was >90%. The patient population in this study was typical of those patients with LIDS. Overall, approximately 50% of patients in each group were Hoehn and Yahr Stage II, approximately 40% Stage III with the remainder Stage IV. Additionally, 90% of all patients were rated as having moderate disease or worse on the CGI-S, consistent with the baseline distribution of UPDRS motor scores. The baseline characteristics (mean+/−SD) are summarized below. There were no statistically significant differences in baseline parameters between the 2 groups.

Nicotine was generally safe and well-tolerated in PD patients with LIDS. Based on the mechanism of action of nicotine, no unexpected AEs occurred. Importantly, nicotine did not worsen, but improved UPDRS total scores.

A total of 11 subjects were withdrawn due to treatment-related AEs: 6 subjects in the nicotine group (1 subject each on 4 mg/day and 8 mg/day, and 2 subjects each in the 16 mg/day and 24 mg/day groups) and 5 subjects in the pbo group. The overall incidence of serious AEs (SAE) was low: 4 subjects in the nicotine group and 2 subjects in the pbo group, respectively. Importantly, all SAEs were assessed as unrelated to study medication. Overall, a higher percentage of subjects reported treatment-related AEs in the nicotine group (54%) compared to the pbo group (20%). The majority of adverse events were mild or moderate in intensity and transient in duration. The most common treatment-emergent AEs in the nicotine group (>5%) were nausea (31%), constipation and dizziness reported by 11% of subjects each, fatigue and non-specific pain reported by 9% of subjects each, and vomiting and nightmares reported by 6% subjects each. The respective incidences in the pbo group were: 3%, 3%, with the remainder 0%. Twenty-nine percent and 3% of subjects used rescue medication in the nicotine and pbo groups, respectively. Mean changes from baseline in blood chemistry, hematology, and vital signs were similar across treatment groups at all study visits. There were no clinically relevant changes in ECG parameters in either group. Serum cotinine levels increased with increasing dose as expected in patients treated with nicotine.

There were no differences in occurrences of impulsivity disorders, as assessed by a positive score on any JayMidi module; reported in 1 subject in each treatment group. Withdrawal symptoms, as assessed by the MNWS-R which has a maximal score of 60, were not a clinically relevant issue. At Week 10 (end of drug treatment) the scores in the nicotine and pbo groups were 7.5 and 6.7, respectively and decreased to 5.4 in the nicotine and 5.2 in the pbo group at end of the follow-up period.

Multiple instruments were used in an exploratory manner to assess the efficacy of nicotine on LIDS. There was a trend or statistically significant improvement in the nicotine group compared to pbo on the majority of patient- and physician-rated outcome measures.

Nicotine resulted in numerical improvement in the UPDRS in the mean change from baseline to Week 10 compared to placebo at every visit during drug treatment. The nicotine group also had a greater mean improvement in the UPDRS Part III score: maximum mean improvement was 2.0 points at Week 10 compared to a mean worsening of −0.4 points in the pbo group (FIG. 1). Importantly, the degree of absolute change from baseline in the nicotine group neared the change that has been considered the minimally clinically relevant change, despite the fact that the drug-treatment period was only 10 weeks in duration and the study was not powered as an efficacy study.

Figure 2:
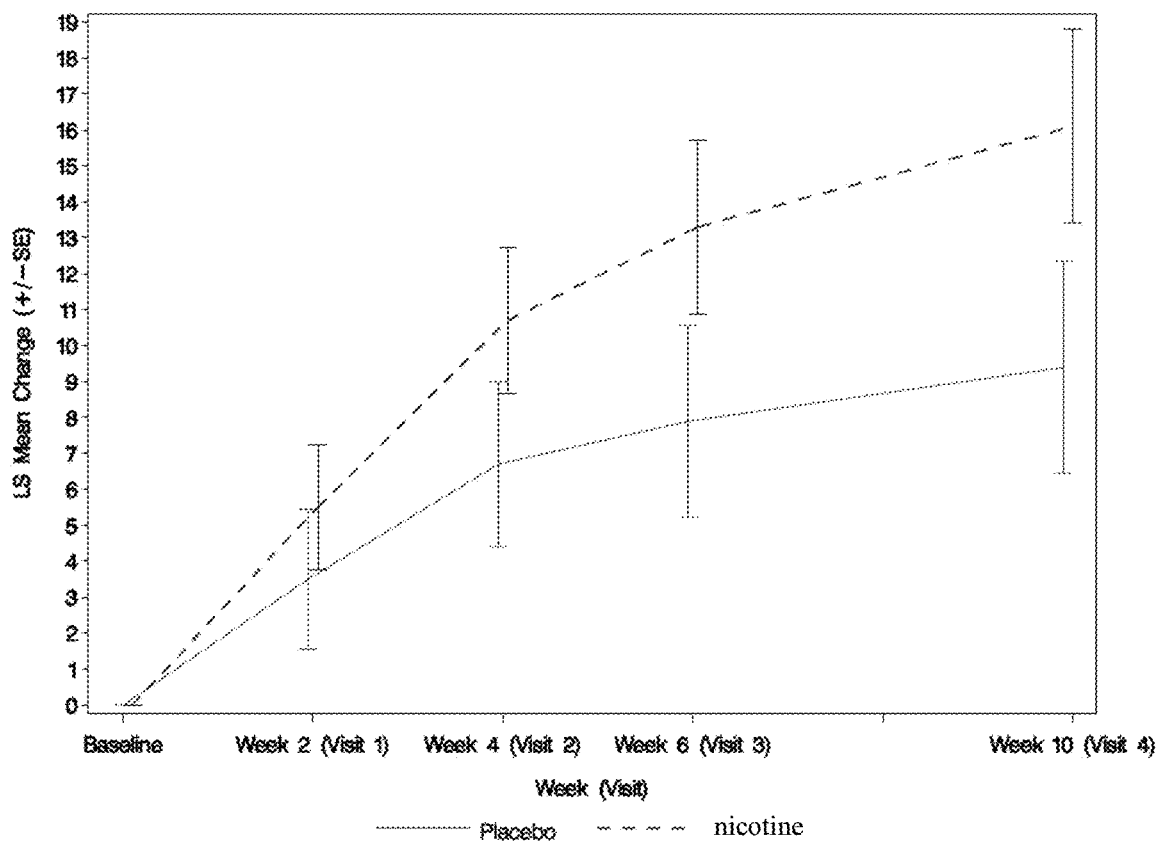
FIG. 2 illustrates mean change from baseline in Unified Dyskiensia Rating Scale Total Score for nicotine compared to placebo.
Figure 3:
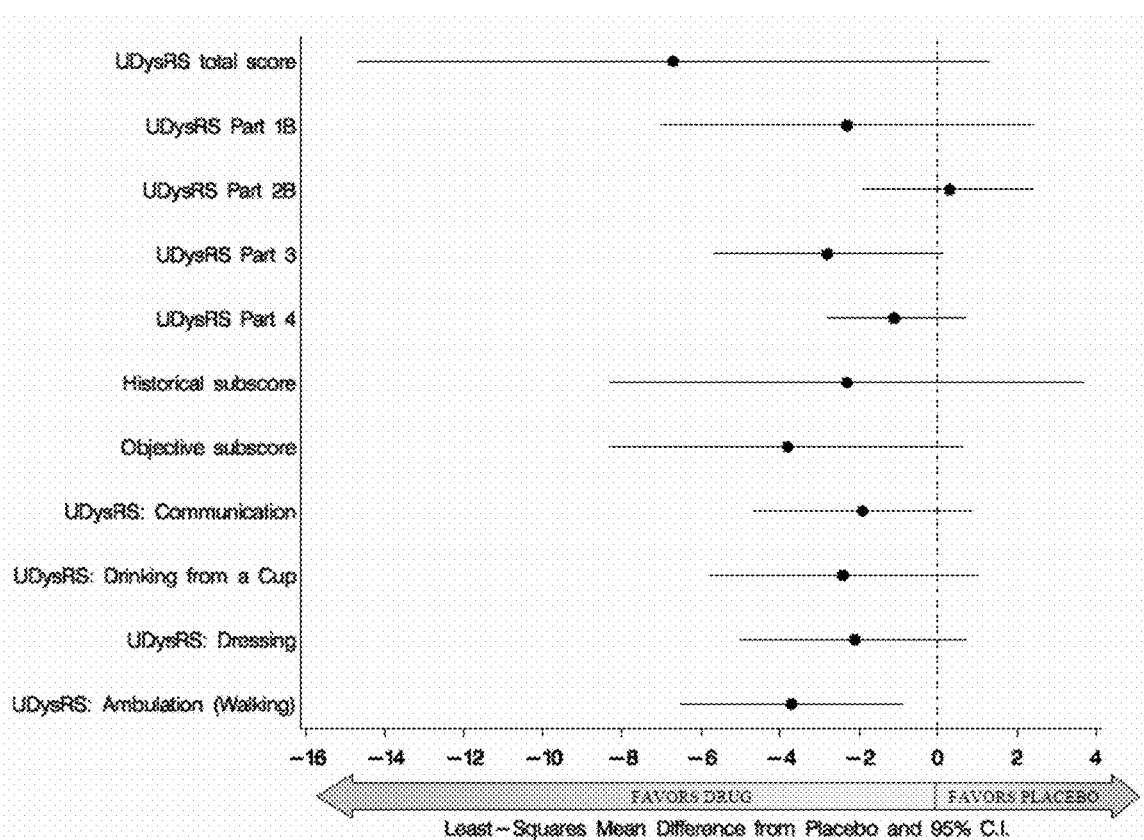
FIG. 3 depicts a forest plot of the Mean Difference between Placebo and nicotine in the change from Baseline to Week 10 of treatment.
Figure 4:
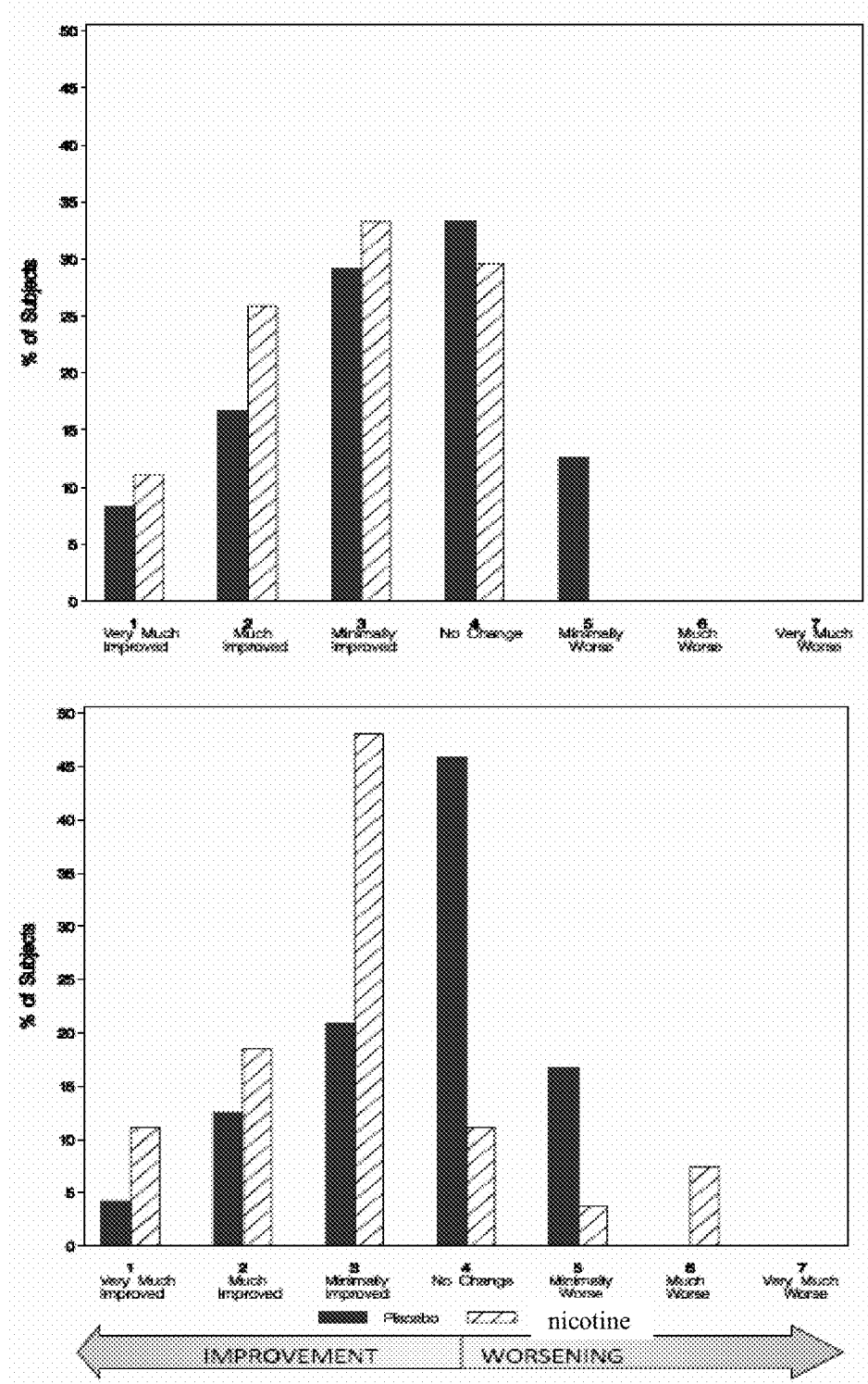
FIG. 4 shows percentage of subjects in each of CGI-C (upper panel) and PGI-C (lower panel) Categories after 10 weeks of treatment.

Similar trends favoring nicotine were also observed on the UDysRS total score as illustrated in FIG. 2. Mean improvement from baseline and greater separation from pbo was observed at every study visit during the drug-treatment period. At Week 10, nicotine resulted in improvement on 9 of 10 subscores of the UDysRS as assessed by the mean changes from baseline compared to pbo, as shown in FIG. 3. Statistically significant improvement in ambulation occurred in those patients treated with nicotine versus pbo (p=0.01). Other statistically significant differences favoring nicotine compared to pbo were observed on the LF-ADL responders and PGI-C responders. At Week 10, 56% of nicotine-treated subjects were responders on the LF-ADL compared to 25% in the pbo group (p=0.04). 78% of patients treated with nicotine rated themselves as having any degree of improvement compared to 38% of pbo-treated subjects (p=0.004, illustrated in FIG. 4). The distribution of nicotine subjects in each category, compared to pbo, was also significant (p=0.02). A similar, but not statistically significant pattern was also seen on the CGI-C.

Example 2: Formulation

Tablets are manufactured using a dry blend process, and hand made on a Carver 'Auto C' Press (Fred Carver, Inc., Indiana). The dry blend process consists of blending all of the ingredients in a plastic bag, and compressing into a 500 mg tablet (10 mg nicotine dose) using a 0.7086".times.0.3937" Mod Oval die (Natoli Engineering).

Tablets include nicotine, PEO Coagulant, Methocel K100M, and magnesium stearate. (PEO Coagulant=poly (ethylene oxide), grade PolyOx Coagulant, NF FP grade, manufactured by Union Carbide/Dow Chemical Company; Methocel K100M=hydroxypropylmethylcellulose, grade Methocel K100M, premium, manufactured by Dow Chemical Company; magnesium stearate, NF, supplied by Spectrum Chemical Company). Amounts of PEO Coagulant range from 10 to 90% by weight, amounts of Methocel K100M range from 10 to 90% by weight, and amounts of magnesium stearate range from 0 to 2% by weight.

The dissolution is determined in USP apparatus I (40 mesh baskets), 100 rpm, in deionized water. Samples, 5 ml at each time-point, are taken without media replacement at 1, 4 and 8 hours.

Example 3: Formulation

Example 2 is repeated with the percentage by weight of inactives as (i) 50% PEO Coagulant, 49% Methocel K100M, and 1% magnesium stearate; (ii) 89% PEO Coagulant, 10% Methocel K100M, and 1% magnesium stearate; and (iii) 10% PEO Coagulant, 89% Methocel K100M, and 1% magnesium stearate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pulsatile release dosage form for twice-daily administration, said form comprising a capsule comprising an effective amount of nicotine for treatment of symptoms of Parkinson's Disease or symptoms associated with dopaminergic treatment of Parkinson's Disease, wherein said capsule is configured to exhibit pulsatile release of said nicotine when administered, the pulsatile release comprising a first peak and a second peak, wherein the first peak occurs within about two hours of administration and the second peak occurs between about two hours and about twelve hours after administration, wherein said capsule comprises a powder comprising nicotine for providing the first release peak upon administration to a patient, and a bead comprising nicotine for providing the second release peak.

2. The dosage form according to claim 1, wherein said bead is selected from the group consisting of enteric-coated beads, erodible-matrix beads, wax-coated beads, ethylcellulose-coated beads, silicone elastomer coated beads, and combinations thereof.

3. The dosage form according to claim 1, wherein said capsule comprises a water-swellable polymeric membrane.

4. The dosage form according to claim 3, wherein said water-swellable polymeric membrane ruptures following administration to a patient.

5. The dosage form according to claim 1, wherein the dosage form is configured to reduce gait and balance problems.

6. The dosage form according to claim 1, wherein the dosage form is configured to reduce levodopa-induced dyskinesias.

7. The dosage form according to claim 1, wherein nicotine is present at less than 10 mg.

8. The dosage form according to claim 1, wherein about 1-2 mg nicotine is released in a first release, and about 2-3 mg nicotine is released in a second release.

9. The dosage form of claim 8, wherein said dosage form is capable of being administered so that one or more metabolites of said nicotine achieves a plasma level of about 1 to about 500 ng/ml within four hours of administration.

10. The dosage form according to claim 1, wherein said dosage form further comprises levodopa, carbidopa, or a combination thereof.

11. The dosage form according to claim 1 wherein nicotine is present at about 10 mg.

12. A method of treating gait and balance problems in a subject, comprising administering an oral composition comprising the pulsatile release dosage form of claim 1, wherein the gait and balance problems are direct symptoms of Parkinson's Disease.

\* \* \* \* \*